United States Patent [19]

Karami

[11] Patent Number: 4,643,728
[45] Date of Patent: Feb. 17, 1987

[54] ELASTICIZED DIAPER WITH WATERPROOF CROTCH SEALS

[75] Inventor: Hamzeh Karami, Tilff, Belgium

[73] Assignee: Colgate Palmolive Company, New York, N.Y.

[21] Appl. No.: 328,293

[22] Filed: Dec. 7, 1981

[51] Int. Cl.[4] ............................................. A61F 13/16
[52] U.S. Cl. .................................. 604/385 A; 604/370
[58] Field of Search ............................. 604/385–386, 604/385.2

[56] References Cited

U.S. PATENT DOCUMENTS

| | | | |
|---|---|---|---|
| 4,050,462 | 9/1977 | Woon et al. | 604/385 |
| 4,226,238 | 10/1980 | Bianco | 604/385 |
| 4,324,245 | 4/1982 | Mesek et al. | 604/385 |
| 4,337,771 | 7/1982 | Pieniak et al. | 604/385 |

*Primary Examiner*—C. Fred Rosenbaum
*Assistant Examiner*—Sherri E. Vinyard
*Attorney, Agent, or Firm*—Herbert S. Sylvester; Murray M. Grill; Norman Blumenkopf

[57] ABSTRACT

A disposable diaper having elasticized waterproof crotch seals formed from waterproof elastic strips secured to the backing sheet and the absorbent pad and under such tension as to eliminate transverse pleats in the crotch area while minimizing the size of the crotch seals about the legs of an infant.

3 Claims, 3 Drawing Figures

ELASTICIZED DIAPER WITH WATERPROOF CROTCH SEALS

BACKGROUND OF THE INVENTION

1. Field of Invention

This invention relates to disposable diapers and more particularly to an elasticized diaper having waterproof crotch seals.

2. Description of the Prior Art

In the past, elasticized contoured diapers have been developed such as that disclosed in the U.S. patent to Buell, No. 3,860,003, issued Jan. 14, 1975 for "Contractable Side Portions for Disposable Diaper" wherein elastic strips are secured to the crotch portions of the diaper and spaced at least ¾ inch from the absorbent pad to form elasticized crotch seals for securement over the legs of the infant to prevent loss of fluid from the interior of the diaper along the legs of the infant. The elasticized strips were placed more than ¾ inch from the absorbent pad in order to prevent pleats forming transversely of the crotch area of the diaper.

Another diaper is presently in production in which the elasticized strips are less than ¾ inch from the absorbent pad for the production of the transverse pleats in the crotch area of the diaper for the purpose of increasing the absorbent capacity at the crotch area of the diaper. However, it has been found that these pleats may act as a channel resulting in excessive diaper leakage and the pleats in the crotch area make the infant's bottom uncomfortable when sitting, especially while the diaper is not saturated.

In each of these prior diapers there is no provision for providing a waterproof seal below the pad between the pad and the backing sheet.

SUMMARY OF THE INVENTION

The present invention overcomes the disadvantages of both of the prior art diapers. Waterproof elastic strips are bonded to the backing sheet and overlie the pad whereby a waterproof crotch seal preventing fluid, which passes through the pad, from leaking toward the edges of the diaper. The waterproof elasticized strips are placed on the pad and means bond the strips to the pad and the backing sheet with the tension on the strips thus maintained so that no transverse pleats are formed in the crotch portion of the diaper thereby reducing leakage and discomfort resulting from the pleats prior to the saturation thereof.

The concept of this invention features a disposable diaper which is contoured in an hour-glass configuration and having an absorbent body between a top sheet and a backing sheet with waterproof elasticized strips bonded to the pad and backing sheet so that the tension on the strips is such that there will be no pleats in the crotch area of the diaper.

DETAILED DESCRIPTION OF THE INVENTION

Figure 1:
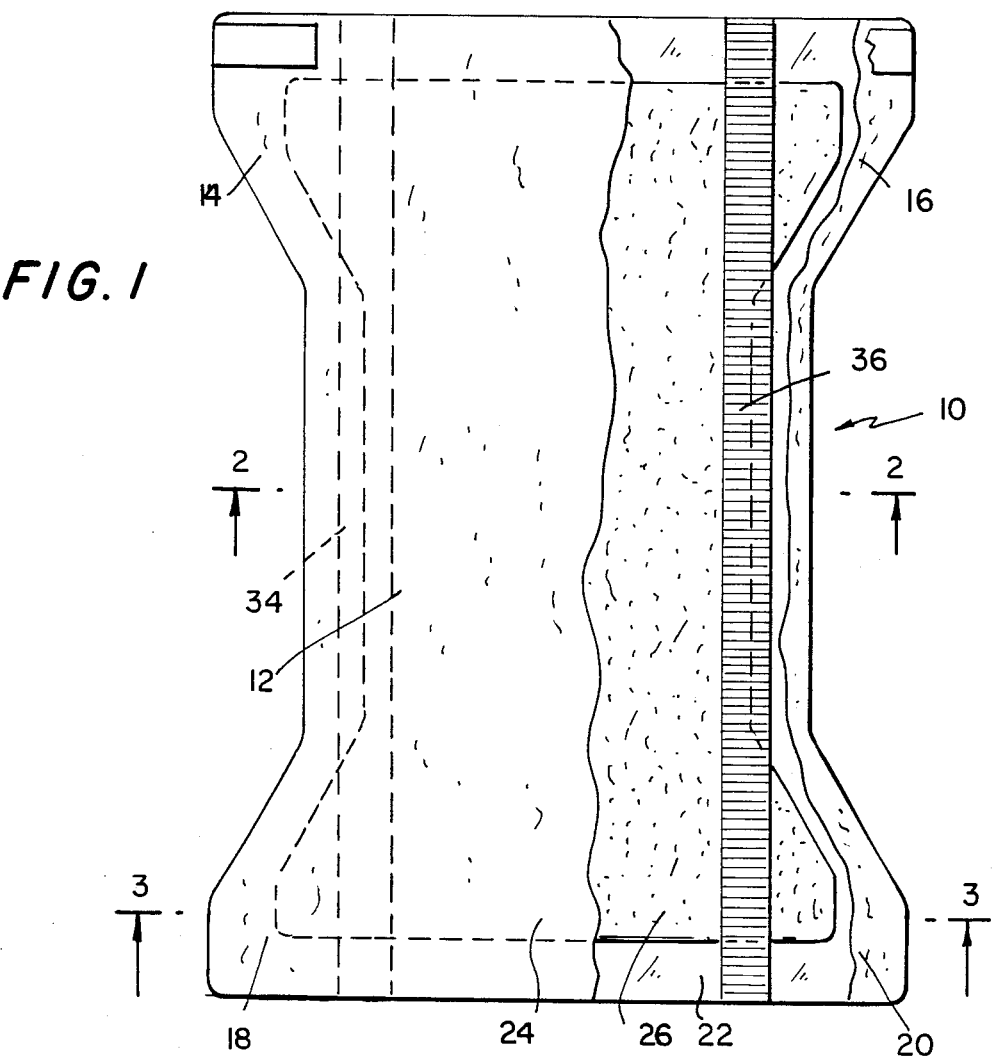
FIG. 1 is a plan view of a diaper constructed in accordance with the concepts of the present invention.
Figure 2:
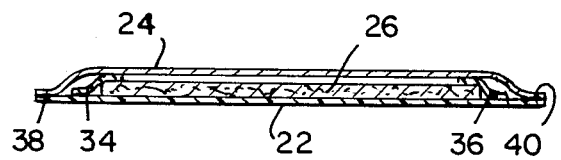
FIG. 2 is a transverse sectional view taken along the plane of line 2—2 in FIG. 1 through the crotch portion of the diaper; and, FIG. 3 is a transverse view taken along the plane of line 3—3 in FIG. 1.
Figure 3:
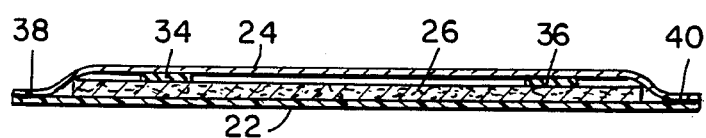

With continuing reference to the accompanying drawing, wherein like reference numerals designate similar parts throughout the various views, reference numeral 10 generally designates an elasticized and contoured disposable diaper constructed in accordance with the concepts of the present invention. The diaper is of an hour-glass configuration having a crotch area 12 and four portions of greater width defining ears 14, 16, 18 and 20. The diaper includes a backing sheet 22 of an impervious polyethylene or polypropylene film. A top sheet 24, preferably of non-woven or polyethylene or polypropylene fibers, is preferably heat sealed by hot melt lines to the backing sheet along the peripheral edges of the diaper. An absorbent pad 26 is disposed between the top sheet 24 and the backing sheet 22 and may be of wood fluff or the like. The pad 26 conforms generally in contour to the hour-glass shape. A pair of elasticized waterproof strips 34 and 36 are provided and are arranged so as to be bonded to form seals 38 and 40 with the backing sheet 22 and are adhesively secured in an overlying relationship relative to the edge of the pad 26. The strips 34 and 36 may extend only the length of the crotch area 12 or may overlie the ears 14, 16, 18 and 20 of the pad. The adhesive serves to secure the strips 34 and 36 under tension so that the tension provided by the elasticized strips is such that pleats are only formed in the crotch seals about the legs of the infant when in use and no pleats are formed in the crotch area 12.

In use, when body fluids pass into the pad 26 and through the pad against the backing sheet these fluids are prevented from passing beyond the periphery of the pad in the crotch area by the seals formed by the strips 34 and 36.

What is claimed is:

1. A disposable diaper comprising a flat backing sheet, an absorbent pad on said backing sheet, said absorbent pad being of an hour-glass shape defining ears spaced from a crotch area, a top sheet overlying said absorbent body, said top sheet being secured to said backing sheet on at least two opposite peripheral edges thereof, opposed elasticized waterproof strips partially overlying and bonded to said pad in said crotch area and having outer portions extending downwardly toward said backing sheet with said outer portions being bonded to said backing sheet to form narrow elasticized crotch seals in the central crotch area portions of said two opposite peripheral edges to define narrow elasticized waterproof seals along the side edges of the crotch portion of said pad, said strips overlying said ears and being bonded to said ears of said pad so that no pleats extend transversely of said crotch area of said pad.

2. A disposable diaper according to claim 1, wherein said top sheet and said backing sheet are bonded together along the peripheral edges thereof.

3. A disposable diaper according to claim 1, wherein said top sheet is heat sealed to said backing sheet.

* * * * *